United States Patent [19]
Homra

[11] Patent Number: 5,915,963
[45] Date of Patent: Jun. 29, 1999

[54] HOLDER FOR ORAL SUCTION DEVICE

[76] Inventor: Ronald A. Homra, 20 Stonehaven Dr., Jackson, Tenn. 38305

[21] Appl. No.: 08/865,214

[22] Filed: May 29, 1997

[51] Int. Cl.[6] .................................................. A61G 15/00
[52] U.S. Cl. .............................................. 433/77; 433/116
[58] Field of Search ................... 433/77, 78, 91, 433/116; 312/209; 604/263

[56]  References Cited

U.S. PATENT DOCUMENTS

| | | | |
|---|---|---|---|
| 2,214,775 | 9/1940 | Pieper | 433/78 |
| 3,198,574 | 8/1965 | Ota et al. | 433/78 |
| 3,802,736 | 4/1974 | Valeska | 433/78 |
| 4,648,839 | 3/1987 | Tiimerdahl et al. | 433/77 |
| 5,161,970 | 11/1992 | Baskas | 433/77 |
| 5,406,939 | 4/1995 | Bala | 206/438 |

*Primary Examiner*—John J. Wilson
*Attorney, Agent, or Firm*—Walker, McKenzie & Walker, P.C.

[57] ABSTRACT

A holder for use with a support member and an oral suction device having a distal end for suctioning a patient's oral cavity. The holder includes a sleeve having an interior and an entrance opening communicating with the interior; and a mount for mounting the sleeve to the support member so that the distal end of the oral suction device can be inserted into the sleeve after the sleeve is mounted to the support member.

20 Claims, 5 Drawing Sheets

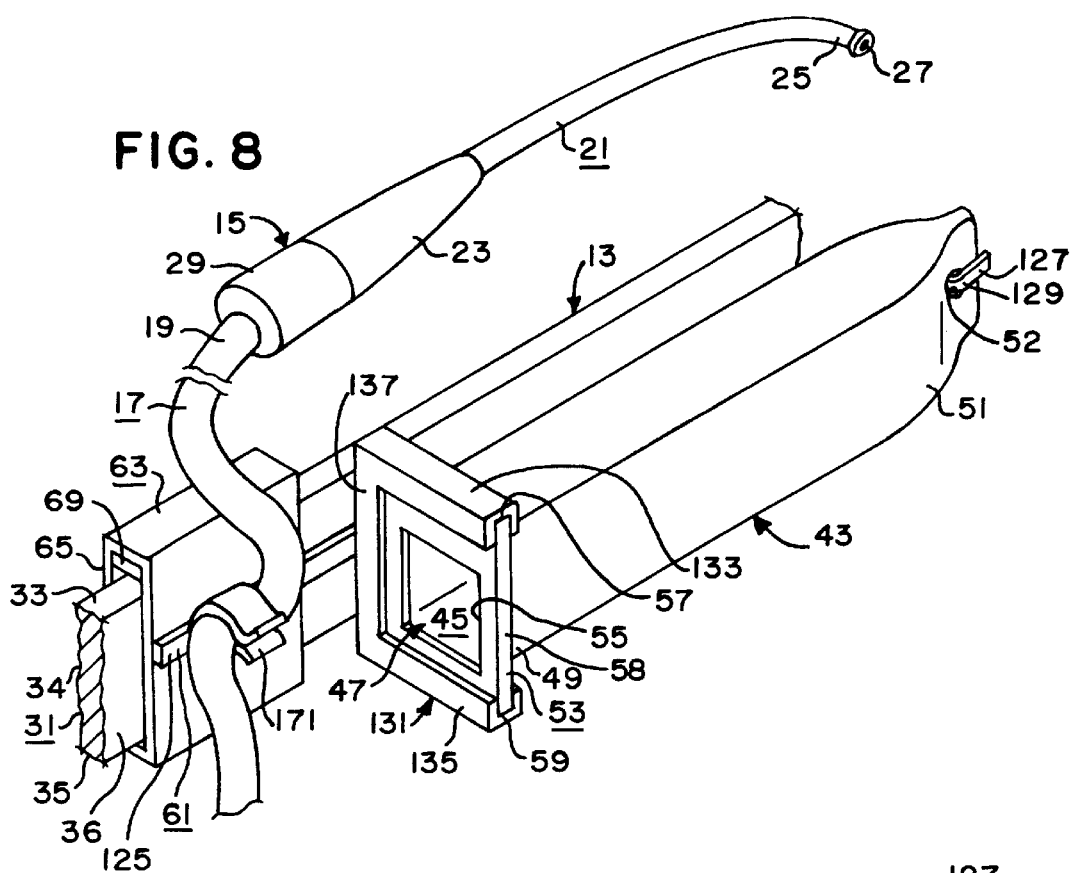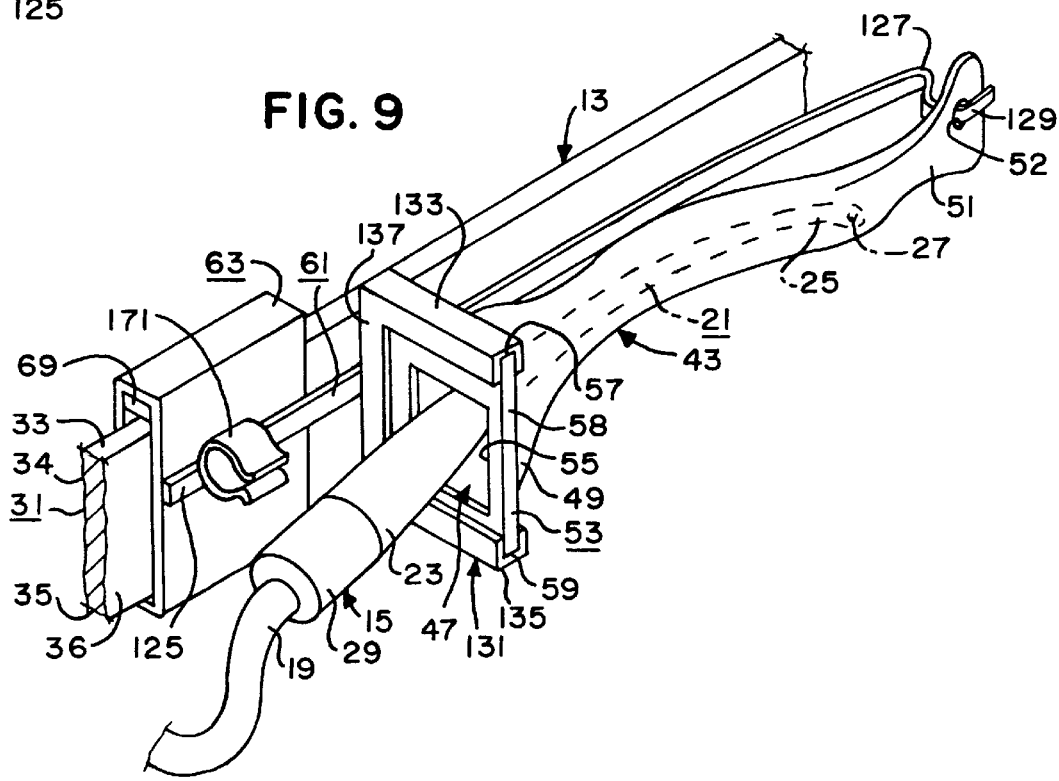

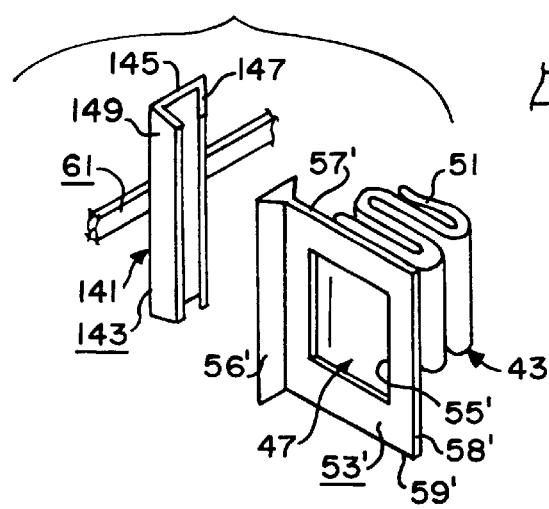
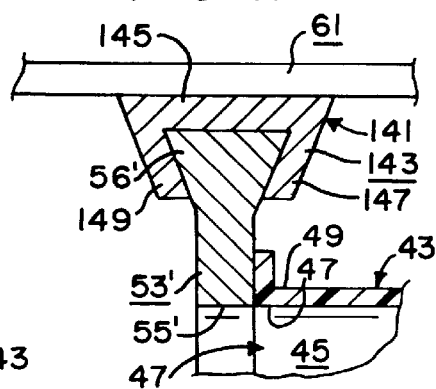
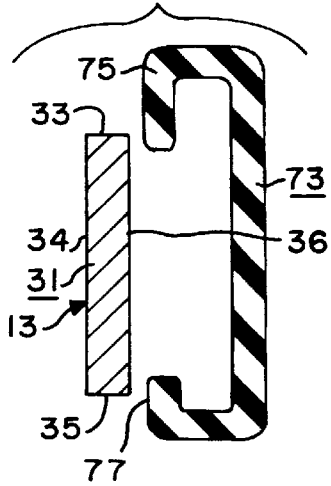
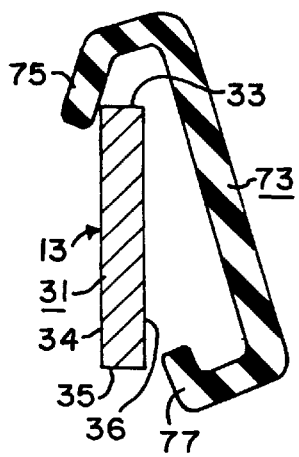
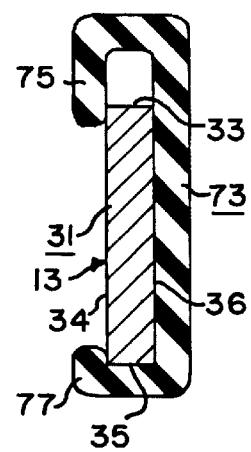
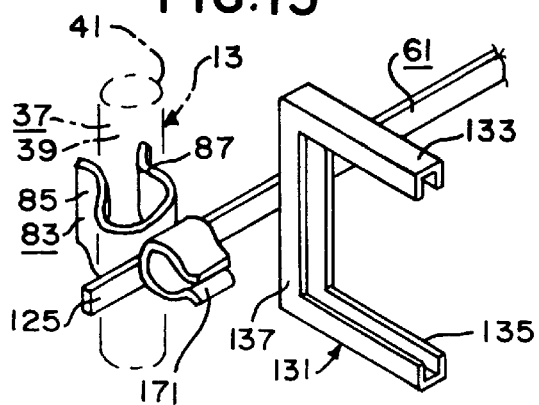
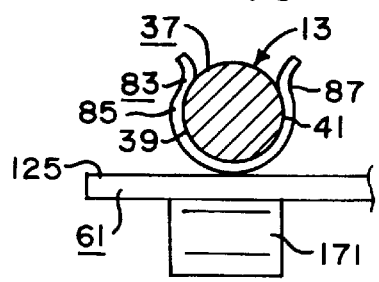

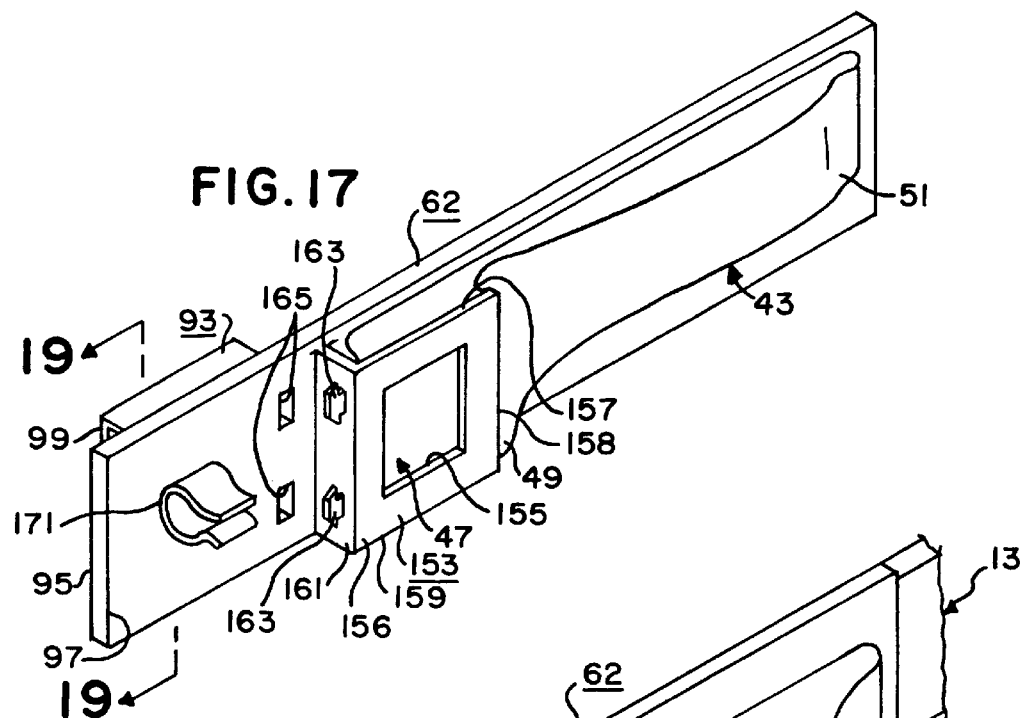
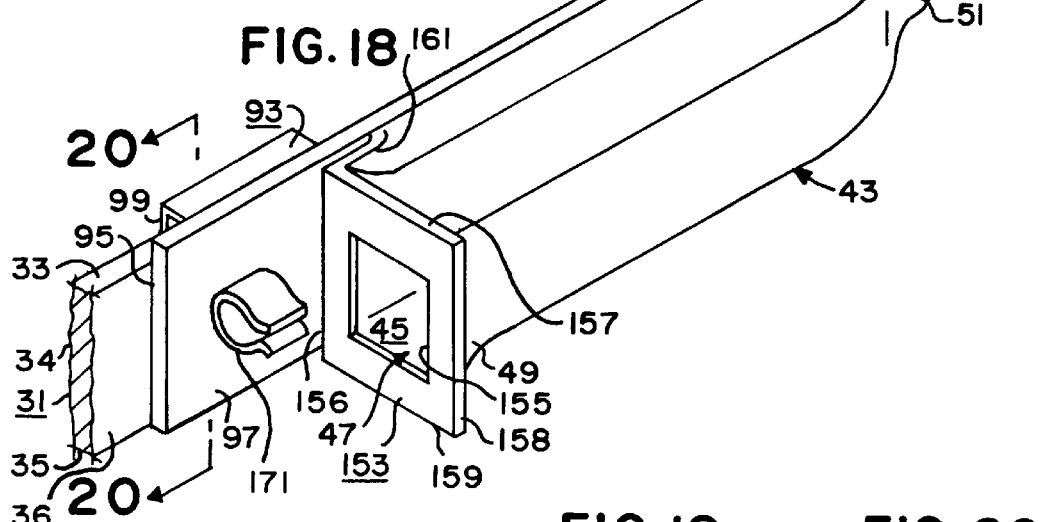
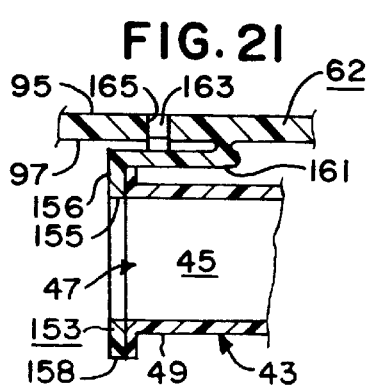
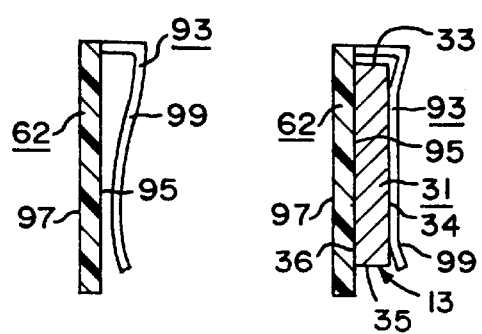

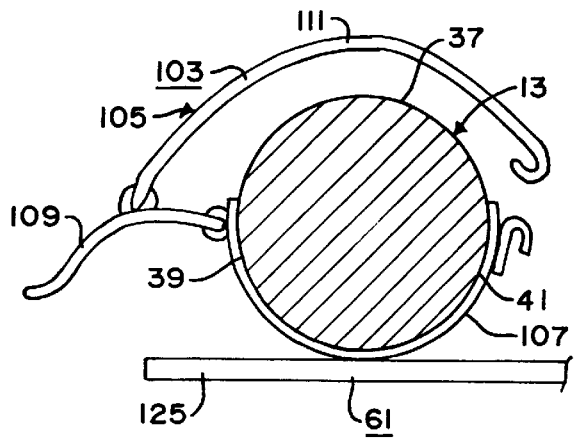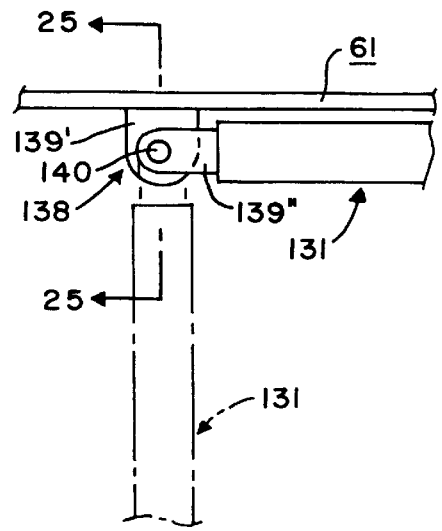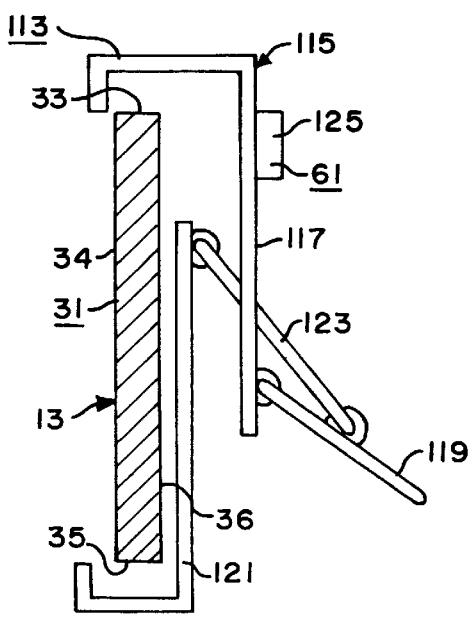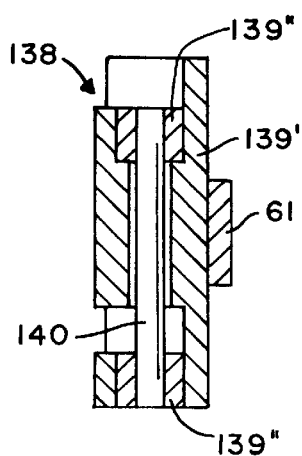

HOLDER FOR ORAL SUCTION DEVICE

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to means for holding an oral suction device during an operation and the like.

2. Information Disclosure Statement

Oral suction devices are commonly used by anesthesiologists and other health care professionals for suctioning fluid, etc., from patient's mouths during operations, while the patient is in intensive care, etc. Such oral suction devices commonly include an elongated, flexible hose having a proximal end for being attached to a vacuum source and a distal end, and a relative rigid suction tube having a proximal end for being attached to the distal end of the hose and a distal end with one or more apertures therein for being inserted into a patient's mouth to suction the oral cavity during surgery, etc. The proximal end of the suction tube preferably has a handle portion provided thereon or formed integrally therewith to allow an anesthesiologist or other health care professional to easily and accurately manipulate the suction tube. Such suction tubes are provided in sterile packages for use during a single operation, etc., and are sold by Sherwood Medical of St. Louis, Mo. 83103, as ARGYLE™ Yankauer Suction Tubes.

A serious problem with the use of such suction tubes is what to do with the tube after its initial use. That is, after a suction tube is first used to suction a patient's mouth, it's exterior surfaces will be covered with body fluid and/or blood, etc., from the patient's mouth. Even if the suction tube is the disposable type, it is generally meant to be used throughout a single operation or procedure. Under current practice, it is typical for an anesthesiologist to initially use a suction tube to suction a patient's mouth and then remove the tube from the patient's mouth and lay the suction tube down on any convenient surface for later use during the same operation. Because of the lack of convenient surfaces, it is common for an anesthesiologist to merely lay the suction tube on the operating bed, or insert the suction tube beneath the edge of the mattress of the operating bed, etc. Such practices can result contamination of the suction tube, the operating bed, and/or operating room personnel, etc.

A preliminary patentability search conducted in class 433, subclasses 91, 97, 60, 77 and 79, and class 604, subclasses 35, 54, 195, 192, 163, 199, 261 and 262, produced the following patents which appear to be relevant to the present invention:

Baskas, U.S. Pat. No. 5,161,970, issued Nov. 10, 1992, discloses a tool holder for mounting on the instrument panel in a dentist's office. The tool holder has a grooved surface for receiving one or more holders for syringes, scalpels, etc. These holders have hexagonal bases for mounting in one of several different positions.

Bala, U.S. Pat. No. 5,406,939, issued Apr. 18, 1995, discloses a protective sheath for an endoscope probe comprising first and second elongated plastic sheets peripherally sealed together at the sides and distal ends thereof, while being unsealed at the proximal ends. The first sheet is transparent and has greater optical clarity than the second sheet, while the second sheet has better frictional slip characteristics than the first sheet.

Nothing in the known prior art discloses or suggests the present invention. More specifically, nothing in the known prior art discloses or suggests an oral suction device holder including a sleeve having an interior and an entrance opening communicating with the interior; and a mount for mounting the sleeve to a support member so that the distal end of the oral suction device can be inserted into the sleeve after the sleeve is mounted to the support member.

BRIEF SUMMARY OF THE INVENTION

The present invention provides a device for holding the distal end of an oral suction device. A basic concept of the present invention is to provide a device that can be mounted to an operating bed or IV pole for holding the distal end of a oral suction device.

The oral suction device holder of the present invention comprises, in general, a sleeve having an interior and an entrance opening communicating with the interior; and a mount for mounting the sleeve to a support member so that the distal end of the oral suction device can be inserted into the sleeve after the sleeve is mounted to the support member.

One object of the present invention is to provide an oral suction device holder which prevents contamination and the spread of viral and bacterial diseases after suctioning the oral cavity while the patient is in the operating room, etc.

Another object of the present invention is to provide such a device which protects hospital personnel, etc., especially anesthesia personnel, from oral secretions.

Another object of the present invention is to provide such a device specifically designed to integrate into the operating room environment when used to suction the oral cavity during surgery.

BRIEF DESCRIPTION OF THE SEVERAL VIEWS OF THE DRAWINGS

FIG. 8 is a perspective view of the oral suction device holder of FIG. 1, shown in combination with the side bar of an operating bed and an oral suction device.

FIG. 9 is a perspective view similar to FIG. 8, but showing the distal end of the suction tube of the oral suction device inserted into the sleeve of the oral suction device holder of FIG. 1.

FIG. 10 is an exploded perspective view of an alternate embodiment of a portion of the oral suction device holder of the present invention.

FIG. 11 is a somewhat diagrammatic sectional view of a portion of the oral suction device holder of FIG. 10, showing the frame of the oral suction device holder of FIG. 10 attached to the frame track thereof.

FIGS. 12, 13 and 14 are somewhat diagrammatic sectional views of an alternate embodiment of a portion of the oral suction device holder, showing how the mount of the oral suction device holder thereof is attached to the side bar of an operating bed.

FIG. 15 is a perspective view of an alternate embodiment of a portion of the oral suction device holder of the present invention.

FIG. 16 is a top plan view of a portion of the embodiment of FIG. 15, shown combined with a standard IV pole or the like.

FIG. 17 is a perspective view of an alternate embodiment of a portion of the oral suction device holder of the present invention, shown in a closed position.

FIG. 18 is a perspective view of the oral suction device holder of FIG. 17, shown in an opened position and in combination with the side bar of an operating bed.

FIG. 19 is a sectional view substantially as taken on line 19—19 of FIG. 17, with portions omitted for clarity.

FIG. 20 is a sectional view substantially as taken on line 20—20 of FIG. 18, with portions omitted for clarity.

FIG. 21 is a sectional view substantially as taken on line 21—21 of FIG. 18, with portions omitted or broken away for clarity.

FIG. 22 is a somewhat diagrammatic view of an alternate clamp of the oral suction device holder of the present invention, shown in combination with a typical IV pole or the like.

FIG. 23 is a somewhat diagrammatic view of another alternate clamp of the oral suction device holder of the present invention, shown in combination with the side bar of an operating bed.

FIG. 24 is a somewhat diagrammatic top plan view of a portion of the oral suction device holder of FIG. 1, showing a modified attachment between the body member and the frame track thereof which allows the frame track to move between a first or in-use position as shown in broken lines in FIG. 24 and a second or stored position as shown in solid lines in FIG. 24.

FIG. 25 is a sectional view substantially as taken on line 25—25 of FIG. 24 with portions thereof omitted for clarity and on a somewhat enlarged scale.

DETAILED DESCRIPTION OF THE INVENTION

Figure 1:
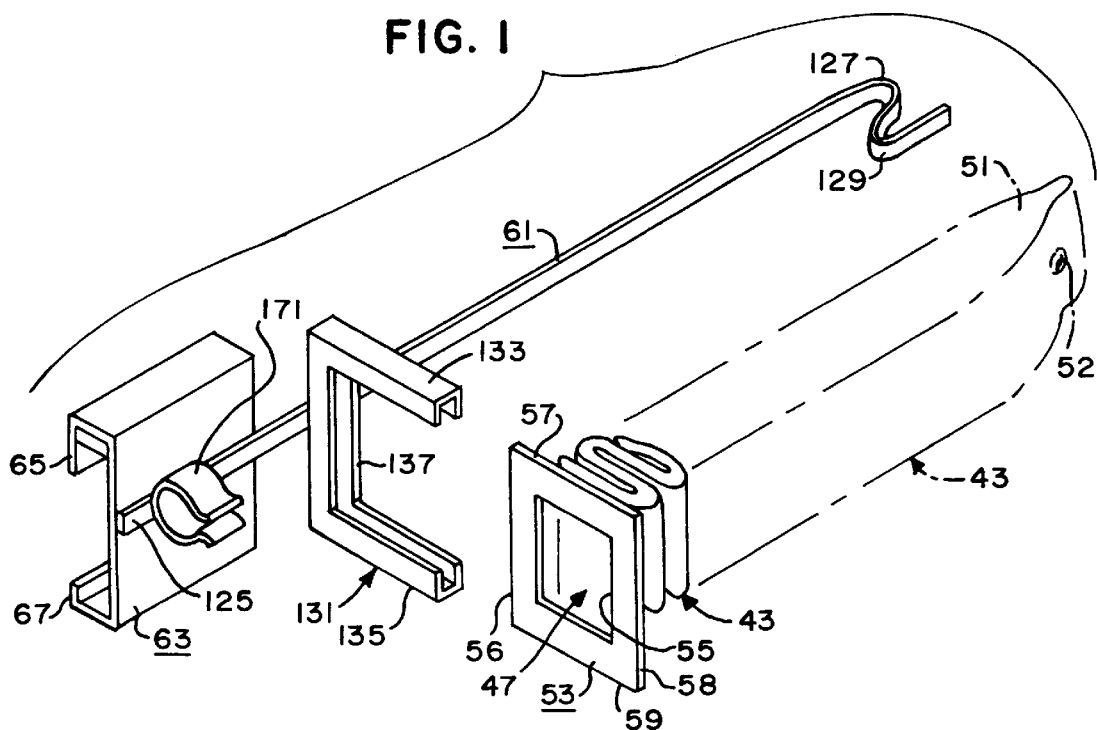
FIG. 1 is an exploded perspective view of a first embodiment of the oral suction device holder of the present invention.
Figure 2:
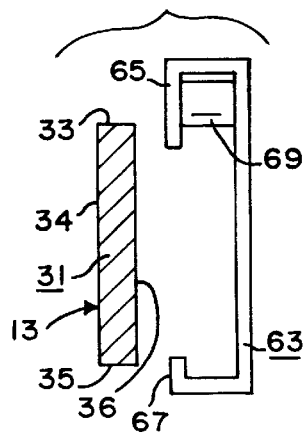
FIGS. 2, 3, 4 and 5 are somewhat diagrammatic side elevational views of a portion of the oral suction device holder of FIG. 1, showing how the mount of the oral suction device holder of FIG. 1 is attached to the side bar of an operating bed.
Figure 3:
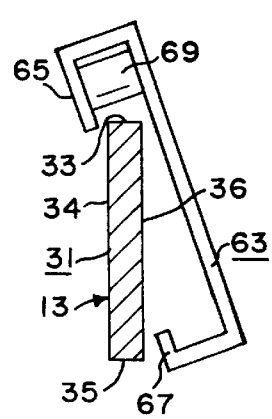
Figure 4:
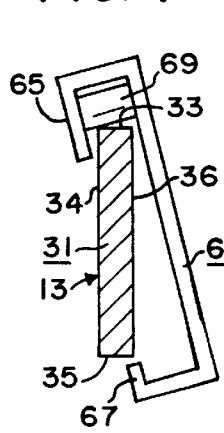

The holder of the present invention is especially designed for use with a support member 13 and an oral suction device 15 such as commonly used by anesthesiologists and other health care professionals for suctioning fluid, etc., from patient's oral cavities during operations, while the patient is in intensive care, etc.

As illustrated in FIGS. 8 and 9, a typical oral suction device 15 commonly includes an elongated, flexible hose 17 having a proximal end (not shown) for being attached to a vacuum source (not shown) and a distal end 19, and a relative rigid suction tube 21 having a proximal end 23 for being attached to the distal end 19 of the hose 17, and a distal end 25 with one or more apertures 27 therein for being inserted into a patient's oral cavity or mouth to suction the patient's oral cavity during surgery, etc. A grip portion or handle 29 is preferably provided at or adjacent, or formed integrally with the proximal end 23 of the suction tube 21 to allow an anesthesiologist or other health care professional to easily and accurately manipulate the suction tube 21. Such suction tubes are provided in sterile packages for use during a single operation, etc., and are sold by Sherwood Medical of St. Louis, Mo. 83103, as ARGYLE™ Yankauer Suction Tubes.

The support member 13 may consist of an elongated support bar 31 (see FIGS. 2–5, 8, 9, 12–14, 18, 20 and 23) that extends along at least a portion of the head of one side of a typical operating bed or the like. A typical support bar 31 is constructed out of a strong, rigid material such as metal, and may have a substantially rectangular cross-sectional area or shape as clearly shown in, for example, FIGS. 2–5. The cross-sectional dimensions of such a typical support bar 31 may be approximately ⅜ inch (0.95 centimeter) wide, and approximately 1⅛ inches (2.86 centimeters) tall. The support bar 31 preferably has a first or upper edge 33 and a second or lower edge 35.

Alternatively, the support member 13 may consist of an elongated pole 37 (see FIGS. 15, 16 and 22) that extends upward from a support surface such as the floor. The pole 37 has a first side 39 and a second side 41, and may consist of a typical I-V pole of any well known construction. The pole 37 is preferably constructed out of a strong, rigid material such as metal, and may have a substantially circular cross-sectional area or shape as clearly shown in FIGS. 15, 16 and 22. The cross-sectional dimensions of such the pole 37 may be the same as a typical I-V pole, e.g., approximately 0.98 inch (2.5 centimeters) in diameter. The pole 37 preferably extends upward from a support base or the like (not shown) that can be stably supported on the floor or the like.

The oral suction device holder of the present invention includes a sleeve having an interior for receiving the distal end 25 of the suction tube 21, and having an entrance opening communicating with the interior for allowing the distal end 25 of the suction tube 21 to be inserted therethrough.

A first embodiment of the sleeve is shown in FIGS. 1, 6, 7, 8 and 9, and identified by the numeral 43. The sleeve 43 has an interior 45 and a mouth or entrance opening 47 communicating with the interior 45 thereof. The sleeve 43 is preferably elongated and has a first or proximal end 49 adjacent the entrance opening 47, and a second or distal end 51 opposite the entrance opening 47. The second end 51 of the sleeve 43 may have an aperture 52 therethrough for reasons which will hereinafter become apparent. The sleeve 43 is preferably constructed of a material that is flexible, and that is impermeable to viral and bacterial contamination. The sleeve 43 may be made of any impermeable plastic, paper or rubber as an elongated tube-like structure having one opened end and one closed end in any manner now apparent to those skilled in the art such as, for example, by being extruded from a plastic material, etc. Due to the flexible nature of the sleeve 43, the sleeve 43 will typically collapse about the distal end 25 of the suction tube 21 as shown in FIG. 9, when the distal end 25 of the suction tube 21 is inserted into the sleeve 43 and vacuum is supplied to the suction tube 21.

The oral suction device holder of the present invention preferably includes a substantially rigid frame attached to the first end of the sleeve.

A first embodiment of the substantially rigid frame is shown in FIGS. 1, 6, 8 and 9, and identified by the numeral 53. The frame 53 is attached to the sleeve 43 about the entrance opening 47 in the sleeve 43. The frame 53 preferably has an opening 55 therethrough communicating with the entrance opening 47 in the sleeve 43 and the interior 45 of the sleeve 43 to allow the distal end 25 of the suction tube 21 to be inserted through the opening 55 in the frame 53, through the entrance opening 47 in the sleeve 43, and into the interior 45 of the sleeve 43. The frame 53 has a first or inner edge 56, a second or upper edge 57, a third or outer edge 58 and a fourth or lower edge 59. The frame 53 is preferably constructed of a material that is rigid, and that is also impermeable to viral and bacterial contamination. The frame 53 may be made of any impermeable, substantially rigid plastic, paper or the like in any manner now apparent to those skilled in the art such as, for example, by being extruded from a plastic material, etc., and glued to, or formed as an one-piece, integral unit with, the first end 49 of the sleeve 43, etc.

A second embodiment of the substantially rigid frame is shown in FIGS. 10 and 11, and identified by the numeral 53'. The frame 53' is substantially similar to the frame 53 and is attached to a sleeve 43 about the entrance opening 47 in the sleeve 43. The frame 53' preferably has an opening 55' therethrough communicating with the entrance opening 47 in the sleeve 43 and the interior 45 of the sleeve 43 to allow the distal end 25 of the suction tube 21 to be inserted through the opening 55' in the frame 53', through the entrance opening 47 in the sleeve 43, and into the interior 45 of the sleeve 43. The frame 53' has a first or inner edge 56', a second or upper edge 57', a third or outer edge 58' and a fourth or lower edge 59'. However, unlike the inner edge 56 of the frame 53, the inner edge 56' of the frame 53' is flanged-shaped for reasons which will hereinafter become apparent. The frame 53' is preferably constructed of a material that is rigid, and that is also impermeable to viral and bacterial contamination. The frame 53' may be made of any impermeable, substantially rigid plastic, paper or the like in any manner now apparent to those skilled in the art such as, for example, by being extruded from a plastic material, etc., and glued to, or formed as an one-piece, integral unit with, the first end 49 of the sleeve 43, etc.

Single or multiple units of the combined sleeve 43 and frame 53 or frame 53' can thus be provided in sterile packages for use by a surgeon, etc.

The oral suction device holder of the present invention includes a mount for mounting a sleeve of the holder to a support member so that the distal end 25 of the suction tube 21 of the oral suction device 15 can be inserted into the sleeve after the sleeve is mounted to the support member. The mount allows a sleeve of the holder to be mounted to the support member 13 so that the distal end 25 of the suction tube 21 of the oral suction device 15 can be easily inserted into and removed from the sleeve after the sleeve is mounted to the support member 13.

The mount preferably includes a body member, and a clamp for clamping the body member to the support member 13.

A first embodiment of the body member is shown in FIGS. 1, 7–10, 15, 16, 22 and 23, and identified by the numeral 61. The body member 61 preferably consist of an elongated, substantially rigid member such as a metal rod or the like as will hereinafter be described in more detail.

A second embodiment of the body member is shown in FIGS. 17–20, and identified by the numeral 62. The body member 62 preferably consists of an elongated, substantially rigid member such as a plastic plate or the like as will hereinafter be described in more detail.

Figure 5:
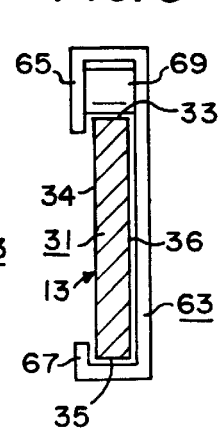
Figure 6:
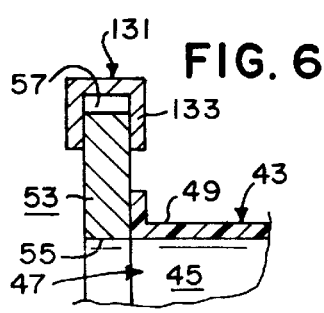
FIG. 6 is a somewhat diagrammatic sectional view of a portion of the oral suction device holder of FIG. 1, showing a portion of a sleeve of the oral suction device holder of FIG. 1 attached to a portion of a frame and frame track thereof.
Figure 7:
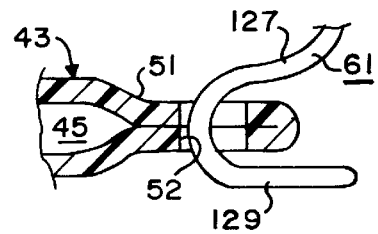
FIG. 7 is a somewhat diagrammatic sectional view of a portion of the oral suction device holder of FIG. 1, showing the distal end of the sleeve of the oral suction device holder of FIG. 1 attached to a body thereof.

A first embodiment of the clamp is shown in FIGS. 1–5, 8 and 9, and identified by the numeral 63. The clamp 63 is especially designed to be removably attached to the support bar 31. Thus, the clamp 63 preferably includes a first finger 65 for fitting over the first edge 33 of the bar 31, and a second finger 67 for fitting over the second edge 35 of the bar 31 to thereby mount the clamp 63 to the bar 31. The clamp 63 preferably includes spring means 69 for fastening the bar 31 of the support member 13 between the first and second fingers 65, 67 thereof. The spring means 69 may consist merely of a leaf spring or the like mounted within the body of the clamp 63 between the first and second fingers 65, 67 thereof for allowing the clamp 63 to be manually inserted over the bar 31 as shown diagrammatically in FIGS. 2–5 so that the spring means 69 can be compressed as the clamp 63 is inserted over the bar 31 and will expand to secure the bar 31 between the first and second fingers 65, 67 after the clamp 63 is fully inserted over the bar 31 as shown in FIG. 5.

A second embodiment of the clamp is shown in FIGS. 12–14, and identified by the numeral 73. The clamp 73 is also especially designed to be removably attached to the support bar 31. Thus, the clamp 73 preferably includes a first finger 75 for fitting over the first edge 33 of the bar 31, and a second finger 77 for fitting over the second edge 35 of the bar 31 to thereby mount the clamp 73 to the bar 31. At least a portion of the clamp 73 is resilient for allowing the first and second fingers 75, 77 to be spread over the first and second edges 33, 35 of the bar 31 as clearly shown in FIGS. 12–14. Thus, at least the first finger 75, and preferably, the entire body of the clamp 73, is preferably molded or otherwise constructed of a somewhat resilient but substantially rigid plastic or the like so that the body of the clamp 73 can be manually inserted over the bar 31 as shown diagrammatically in FIGS. 12–14 with the first finger 75 being spread away from the second finger 77 somewhat as the clamp 73 is inserted over the bar 31. The first finger 75 will then spring back to its normal position after the clamp 73 is fully inserted over the bar 31 as shown in FIG. 14 to thereby secure the mount to the bar 31 as will now be apparent to those skilled in the art.

A third embodiment of the clamp is shown in FIGS. 15 and 16, and identified by the numeral 83. The clamp 83 is especially designed to be removably attached to the support pole 37. The clamp 83 preferably consist of a spring member having a first finger 85 for clamping over the first side 39 of the bar 37, and a second finger 87 for clamping over the second side 41 of the pole 37 to thereby mount the clamp 83 to the pole 37. At least a portion of the clamp 83 is resilient for allowing the first and second fingers 85, 87 to be spread over the first and second sides 39, 41 of the pole 37 as clearly shown in FIGS. 15 and 16. Thus, the entire body of the clamp 83 is preferably pressed or otherwise constructed of a somewhat resilient but substantially rigid spring metal or the like so that the clamp 83 can be manually inserted over the pole 37 with the first and second fingers 85, 87 spreading away from one another somewhat as the clamp 83 is inserted over the pole 37, and the springing back toward one another to their normal position after the clamp 83 is fully inserted over the bar 31 as shown in FIG. 16 to thereby secure the mount to the pole 37 as will now be apparent to those skilled in the art.

A fourth embodiment of the clamp is shown in FIGS. 17, 18, 19 and 20, and identified by the numeral 93. The clamp 93 is also especially designed to be removably attached to the support bar 31, and is especially designed for use with the body member 62. The body member 62 preferably includes a substantially flat first or inner face 95, and a substantially flat second or outer face 97. The clamp 93 preferably includes a finger 99 for fitting over the first edge 33 of the bar 31 and for engaging the first face 34 of the bar 31 to springably clamp the bar 31 between the finger 99 and the first face 95 of the body member 62 as clearly shown in FIG. 20. At least a portion of the clamp 93 is resilient for allowing the finger 99 to be spread over the first edge 33 of the bar 31. Thus, at least the finger 99 is preferably molded or otherwise constructed of a somewhat resilient but substantially rigid metal, plastic or the like so that the finger 99 of the clamp 93 can be manually inserted over the bar 31 with the finger 99 being spread away from the first face 95 of the body member 62 somewhat as the clamp 93 is inserted over the bar 31. The finger 99 will then spring back to its normal position after the clamp 93 is fully inserted over the bar 31 as shown in FIG. 20 to thereby clamp the bar 31 between the finger 99 and the first face 95 of the body member 62 as will now be apparent to those skilled in the art.

A fifth embodiment of the clamp is shown in FIG. 22, and identified by the numeral 103. The clamp 103 is also especially designed to be removably attached to the support pole 37. The clamp 103 preferably includes a lever-type clasp 105 for securing to the pole 37. The clasp 105 may include a first member 107 attached to the body member 61 for extending around approximately half of the diameter of the pole 37, a lever 109 pivotally attached to one end of the first member 107, and a second member 111 pivotally attached at one end to a midportion of the lever 109 and hookably attachable at the other end to the end of the first member 107 opposite the lever 109 so that the clasp can be securely clamped about the pole 37 by merely placing the first member 107 around a portion of the pole 37, hooking the distal end of the second member 111 to the distal end of the first member 107, and then closing the lever 109 to draw the first and second members 107, 109 against the pole 37 as will now be apparent to those skilled in the art.

A sixth embodiment of the clamp is shown in FIG. 23, and identified by the numeral 113. The clamp 113 is also especially designed to be removably attached to the support bar 31. Thus, the clamp 113 preferably includes a lever-type clasp 115 for securing to the bar 31. The clasp 115 may include a first member 117 attached to the body member 61, etc., and having a hook-like distal end for hooking over the first edge 33 of the bar 31, a lever 119 pivotally attached to the proximal end of the first member 117, a second member 121 having a hook-like distal end for hooking over the second edge 35 of the bar 31, and a link member 123 pivotally attached at one end to a midportion of the lever 119 and pivotally attached at the other end to the end of the proximal end of the second member 121 so that the clasp can be securely clamped about the bar 31 by merely placing hook-like ends of the first and second members 117, 121 around the opposite edges 33, 35 of the bar 31, and then closing the lever 119 to draw the distal ends of the first and second members 117, 121 against the bar 31 as will now be apparent to those skilled in the art.

As stated hereinabove, the body member 61 preferably consist of an elongated, substantially rigid member such as a metal rod or the like. Thus, the body member 61 includes a first end 125 and a second end 127. The second end 127 of the body member 61 preferably terminates in a hook or hook-like member 129 for allowing the second end 51 of the sleeve 43 to be hooked thereonto. More specifically, the hook 129 is preferably especially designed to extend through the aperture 52 in the second end 51 of the sleeve 43 as clearly shown in FIGS. 7–9 to removably secure the second end 51 of the sleeve 43 to the second end 127 of the body member 61. The clamps 63, 73, 83, 103, 113 are preferably rigidly attached to a respective body member 61 adjacent the first end 125 thereof by welding, glue, bolts, etc., as will now be understood by those skilled in the art.

The oral suction device holder of the present invention may include a frame track for attaching the frame 53 to the mount.

A first embodiment of the frame track is shown in FIGS. 1, 6 8, 9 and 15, and identified by the numeral 131. The frame track 131 preferably includes an upper track member 133 for receiving the upper edge 57 of the frame 53, and a lower track member 135 for receiving the lower edge 59 of the frame 53. In addition, the frame track 131 may include an inner track member 137 for receiving the inner edge 56 of the frame 53. Each track member 133, 135, 137 preferably has a groove therein to allow the respective edges 56, 57, 59 of the frame 53 to be easily slide thereinto as will now be apparent to those skilled in the art. More specifically, each track member 133, 135, 137 may be substantially U-shaped in cross-section. The frame track 131 may be molded, stamped or otherwise manufactured out of a substantially rigid metal or plastic, etc., as welded, glued, bolted or otherwise fixedly attached to the body member 61 a spaced distance from the second end 127 of the body member 61 to allow the sleeve 43 to fully extend when the first end 49 thereof is attached via the frame 53 to the frame track 131 and the second end 51 thereof is attached via the hook 129 to the second end 127 of the body member 61.

A modified attachment between the frame track 131 and the body member 61 is shown in FIGS. 24 and 25. This modified attachment includes a hinge 138 attaching the frame track 131 to the body member 61 in a manner which allows the frame track 131 to pivot between a first or in-use position located substantially perpendicular to the body member 61 as shown in broken lines in FIG. 24 and a second or stored position located substantially parallel to the body member 61 as shown in solid lines in FIG. 24. The hinge 138 may include typical structure, such as a first knuckle 139' attached to the body member 61 by welding or the like, a second knuckle or set of knuckles 139" attached to the frame track 131 by welding or the like, and a pivot rod or axle 140 pivotally joining the first and second knuckles 139', 139" in such a manner to allow the frame track 131 to be moved between the fist and second positions. In addition, the hinge 138 may be modified and/or include structure, such as cut-outs in the knuckles, springs (not shown), etc., for allowing the frame track 131 to be manually locked in the first or second positions and for biasing the frame track 131 to the first or second position, etc., as will now be apparent to those skilled in the art.

A second embodiment of the frame track is shown in FIGS. 10 and 11, and identified by the numeral 141. The frame track 141 preferably includes an inner track member 143 for especially designed to receive the flange-like inner edge 56' of the frame 53'. More specifically, the inner track member 143 preferably includes a back wall 145, a first side wall 147 extending outward from one side edge of the back wall 145, and a second side wall 149 extending outward from the other side edge of the back wall 145, with the side walls 147, 149 angled inward toward one another as they extend from the back wall 145 as clearly shown in FIGS. 10 and 11 to grip the flange-like inner edge 56' of the frame 53' when the flange-like inner edge 56' is slid thereinto as will now be apparent to those skilled in the art. The side walls 147, 149 are preferably springable toward and away from one another so that the flange-like inner edge 56' of the frame 53' can be securely gripped thereby. The frame track 141 may be molded, stamped or otherwise manufactured out of a substantially rigid metal or plastic, etc., and welded, glued, bolted or otherwise fixedly attached to the body member 61 a spaced distance from the second end 127 of the body member 61 to allow the sleeve 43 to fully extend when the first end 49 thereof is attached via the frame 53 to the frame track 141 and the second end 51 thereof is attached via the hook 129 to the second end 127 of the body member 61.

As stated hereinabove, the body member 62 preferably consist of an elongated, substantially rigid member such as a plastic plate or the like including a substantially flat first or inner face 95 and a substantially flat second or outer face 97. A third embodiment of the substantially rigid frame is shown in FIGS. 17, 18 and 21, especially designed and constructed for use with the body member 62, and identified by the numeral 153. The frame 153 is substantially similar to the frame 53 and is attached to a sleeve 43 about the entrance opening 47 in the sleeve 43. The frame 153 preferably has an opening 155 therethrough communicating with the entrance opening 47 in the sleeve 43 and the interior 45 of the sleeve 43 to allow the distal end 25 of the suction tube 21 to be inserted through the opening 155 in the frame 153, through the entrance opening 47 in the sleeve 43, and into the interior 45 of the sleeve 43. The frame 153 has a first or inner edge 156, a second or upper edge 157, a third or outer edge 158 and a fourth or lower edge 159. The frame 153 is preferably constructed of a material that is rigid, and that is also impermeable to viral and bacterial contamination. The frame 153 may be made of any impermeable, substantially rigid plastic, paper or the like in any manner now apparent to those skilled in the art such as, for example, by being extruded from a plastic material, etc., and glued to, or formed as an one-piece, integral unit with, the first end 49 of the sleeve 43, etc. However, unlike the frame 53, the inner edge 156 of the frame 153 is preferably attached to the body member 62 by way of a hinge member 161. The hinge member 161 may consist of a flexible tab or the like molded or otherwise attached to both the first edge 156 of the frame 153 and the body member 62 to provide a hinge to allow the frame 153 to be manually moved from a closed, stored position as shown in FIG. 17, to an opened, ready-for-use position as shown in FIGS. 18 and 21. Preferably, the body member 62, clamp 93, frame 153, and hinge member 161 are molded or otherwise formed out of a plastic material or the like as an integral, one-piece unit. Means, such as coacting tabs 163 and slots 165 are preferably provided to allow the frame 153 to be locked in the opened, ready-for-use position as will now be apparent to those skilled in the art. In this self-contained embodiment, the second end 51 of the sleeve 43 may be glued or otherwise permanently attached to the second end of the body member 62 rather than being removably attached thereto via a hook-and-aperture arrangement as shown with respect to the body member 61.

The oral suction device holder of the present invention may include a clamp 171 for allowing the flexible hose 17 of the oral suction device 15 to be clamped thereto when desired. The clamp 171 preferably consists of a typical spring-type pinch or squeeze clamp well known to those skilled in the art for being glued, bolted or otherwise securely attached to a respective body member 61, 62 in a position to allow the user of the oral suction device 15 to easily insert a portion of the flexible hose 17 therein when using the oral suction device holder of the present invention.

Although the present invention has been described and illustrated with respect to preferred embodiments and preferred uses therefor, it is not to be so limited since modifications and changes can be made therein which are within the full intended scope of the invention.

I claim:

1. A holder for use with a support member and an oral suction device having a distal end for suctioning a patient's oral cavity: the holder comprising:
   (a) a flexible sleeve having an interior and an entrance opening communicating with the interior;
   (b) a mount for mounting the sleeve to the support member so that the distal end of the oral suction device can be inserted into the sleeve after the sleeve is mounted to the support member; and
   (c) a substantially rigid frame attached to the sleeve about the entrance opening in the sleeve, the frame having an opening therethrough communicating with the entrance opening in the sleeve and the interior of the sleeve.

2. The holder of claim 1 in which the sleeve is constructed of a material that is impermeable to viral and bacterial contamination.

3. The holder of claim 1 in which the mount includes a clamp for clamping onto the support member.

4. The holder of claim 3 in which the support member includes a bar with a first edge and a second edge; and in which the clamp includes a first finger for fitting over the first edge of the bar of the support member, and includes a second finger for fitting over the second edge of the bar of the support member.

5. The holder of claim 4 in which the clamp includes spring means for fastening the bar of the support member between the first and second fingers of the clamp.

6. The holder of claim 4 in which at least a portion of the clamp is resilient for allowing the first and second fingers of the clamp to be spread over the first and second edges of the bar of the support member.

7. The holder of claim 4 in which the clamp includes a lever-type clasp for securing the first and second fingers to the bar of the support member.

8. The holder of claim 3 in which the support member includes a pole having opposite first and second sides; and in which the mount includes a first finger for clamping over the first side of the pole, and a second finger for clamping over the second side of the pole.

9. The holder of claim 8 in which the clamp includes a lever-type clasp for securing the first and second fingers to the pole of the support member.

10. The holder of claim 1 in which is included a frame track for attaching the frame to the mount.

11. The holder of claim 10 in which the frame has an upper edge and a lower edge; and in which the frame track includes an upper track member for receiving the upper edge of the frame and includes a lower track member for receiving the lower edge of the frame.

12. The holder of claim 10 in which the frame has an inner edge; and in which the frame track includes a track member for receiving the inner edge of the frame.

13. The holder of claim 12 in which the inner edge of the frame has a flange portion; and in which the track member of the frame track includes a slot for receiving the flange portion of the inner edge of the frame.

14. The holder of claim 10 in which the mount includes an elongated body; in which the sleeve is elongated and has a first end for attachment to the body, and has a second end for attachment to the frame; and in which the frame track is attached to the body at a location to position the second end of the sleeve remote from the first end of the sleeve.

15. The holder of claim 1 in which the mount includes an elongated body; in which the sleeve is elongated and has a first end for attachment to the body, and has a second end for attachment to the body remote from the first end.

16. The holder of claim 15 in which the body has a hook-like member at one end thereof; and in which the first end of the sleeve is adapted to be hooked onto the hook-like member of the body.

17. The holder of claim 1 in which the mount includes an elongated body; in which the sleeve is elongated and has a first end for attachment to the body, and has a second end for attachment to the frame; and in which the frame is attached to the body at a location to position the second end of the sleeve remote from the first end of the sleeve.

18. The holder of claim 17 in which the frame is pivotally attached to the body for movement between an stored position and an in-use position.

19. A holder for use with a support member and an oral suction device having a distal end for suctioning a patient's oral cavity; the holder comprising:

(a) an elongated, flexible sleeve having first and second ends, having an interior, and having an entrance opening communicating with the interior;

(b) a substantially rigid frame attached to the sleeve about the entrance opening in the sleeve; the frame having an opening therethrough communicating with the entrance opening in the sleeve and the interior of the sleeve; and (c) a mount for mounting the frame and the sleeve to the support member so that the distal end of the oral suction device can be inserted into the sleeve after the sleeve is mounted to the support member; the mount including a clamp for clamping onto the support member and including an elongated body having first and second ends with the first end of the sleeve attached to the second end of the body and with the frame attached adjacent the second end of the body.

20. A holder for use with a support member and an oral suction device having a distal end for suctioning a patient's oral cavity; the holder comprising:

(a) a sleeve having an interior and an entrance opening communicating with the interior, and in which at least a portion of the sleeve is flexible;

(b) a mount for mounting the sleeve to the support member so that the distal end of the oral suction device can be inserted into the sleeve after the sleeve is mounted to the support member; and (c) a frame attached to the sleeve for holding the entrance opening of the sleeve opened.

* * * * *

UNITED STATES PATENT AND TRADEMARK OFFICE
CERTIFICATE OF CORRECTION

PATENT NO : 5,915,963
DATED : June 29, 1999
INVENTOR(S): Dr. Ronald A. Homra

It is certified that error appears in the above-identified patent and that said Letters Patent is hereby corrected as shown below:

On the title page, column one, item 76: "20 Stonehaven Dr." should be --65 Stonehaven Dr.-- as the inventor's address Signed and Sealed this Twenty-seventh Day of March, 2001

*Attest:*

NICHOLAS P. GODICI

*Attesting Officer*  *Acting Director of the United States Patent and Trademark Office*